US009737348B2

United States Patent
Zeetser et al.

(10) Patent No.: US 9,737,348 B2
(45) Date of Patent: *Aug. 22, 2017

(54) METHOD AND DEVICE FOR CORRECTING BONE DEFORMITIES

(71) Applicant: FastForward Surgical Inc., Henderson, NV (US)

(72) Inventors: Vladimir Zeetser, Tarzana, CA (US); Dawn Buratti, Malibu, CA (US)

(73) Assignee: FastForward Surgical Inc., Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/599,362

(22) Filed: Jan. 16, 2015

(65) Prior Publication Data

US 2015/0282849 A1 Oct. 8, 2015

Related U.S. Application Data

(63) Continuation of application No. PCT/US2013/050687, filed on Jul. 16, 2013, which is
(Continued)

(51) Int. Cl.
*A61B 17/80* (2006.01)
*A61B 17/86* (2006.01)
*A61B 17/82* (2006.01)

(52) U.S. Cl.
CPC ...... *A61B 17/8061* (2013.01); *A61B 17/8033* (2013.01); *A61B 17/8085* (2013.01);
(Continued)

(58) Field of Classification Search
CPC .......... A61B 17/80; A61B 17/8033; A61B 17/8038; A61B 17/8042; A61B 17/8047;
(Continued)

(56) References Cited

U.S. PATENT DOCUMENTS 1,665,030 A 4/1928 Hartwig
1,746,865 A 2/1930 Page
(Continued)

FOREIGN PATENT DOCUMENTS

WO WO 2008/019511 2/2008
WO WO 2009/086397 7/2009

OTHER PUBLICATIONS

Sep. 6, 2013 International Search Report and Written Opinion for International Application No. PCT/US2013/050687 Filed Jul. 16, 2013.
(Continued)

*Primary Examiner* — Si Ming Ku
(74) *Attorney, Agent, or Firm* — Knobbe, Martens, Olson & Bear LLP

(57) ABSTRACT

The present invention is a method and device for the correction and reduction of bone deformities, such as metatarsus primus adductus, using a plate body with winged buttresses and dorsal loop. The method and device can be affixed to a bone without any drilling or violating of the bone and can use a tethering technique which does not require drilling into the second metatarsal, nor does it require the placement of a prominent suture knot/button device medially along the first metatarsal.

10 Claims, 6 Drawing Sheets

Related U.S. Application Data a continuation of application No. 13/720,826, filed on Dec. 19, 2012, now Pat. No. 8,998,904.

(60) Provisional application No. 61/672,297, filed on Jul. 17, 2012, provisional application No. 61/713,443, filed on Oct. 12, 2012.

(52) U.S. Cl.
CPC .............. *A61B 17/82* (2013.01); *A61B 17/86* (2013.01); *Y10S 606/902* (2013.01); *Y10S 606/906* (2013.01)

(58) Field of Classification Search
CPC ... A61B 17/8061; A61B 17/82; A61B 17/842; A61F 2/42; A61F 2/4225; A61F 2/4241
See application file for complete search history.

(56) References Cited

U.S. PATENT DOCUMENTS

| | | | |
|---|---|---|---|
| 2,596,038 | A | 5/1952 | Mayer |
| 2,706,023 | A | 4/1955 | Merritt |
| 2,958,324 | A | 11/1960 | Berkemann |
| 4,583,303 | A | 4/1986 | Laiacona et al. |
| 4,644,940 | A | 2/1987 | Nakamura |
| 5,190,545 | A | 3/1993 | Corsi et al. |
| 5,222,977 | A | 6/1993 | Esser |
| 5,282,782 | A | 2/1994 | Kasahara |
| 5,529,075 | A | 6/1996 | Clark |
| 5,743,913 | A | 4/1998 | Wellisz |
| 5,843,085 | A | 12/1998 | Graser |
| 6,318,373 | B1 | 11/2001 | Kasahara |
| 6,391,031 | B1 | 5/2002 | Toomey |
| 6,520,965 | B2 | 2/2003 | Chervitz et al. |
| 6,629,943 | B1 | 10/2003 | Schroder |
| 6,746,450 | B1 | 6/2004 | Wall et al. |
| 6,964,645 | B1 | 11/2005 | Smits |
| 7,344,538 | B2 | 3/2008 | Myerson et al. |
| 7,582,088 | B2 | 9/2009 | Marissen et al. |
| 7,875,058 | B2 | 1/2011 | Holmes |
| 7,901,431 | B2 | 3/2011 | Shumas |
| 8,057,522 | B2 | 11/2011 | Rothman et al. |
| 8,221,455 | B2 | 7/2012 | Shumas |
| 8,257,403 | B2 | 9/2012 | Den Hartog et al. |
| 8,257,406 | B2 | 9/2012 | Kay et al. |
| 8,398,678 | B2 | 3/2013 | Baker et al. |
| 2004/0127907 | A1 | 7/2004 | Dakin et al. |
| 2005/0021033 | A1 | 1/2005 | Zeiler et al. |
| 2005/0049593 | A1 | 3/2005 | Duong et al. |
| 2006/0241607 | A1 | 10/2006 | Myerson et al. |
| 2006/0241608 | A1 | 10/2006 | Myerson et al. |
| 2008/0008777 | A1 | 1/2008 | Radovic |
| 2008/0155731 | A1 | 7/2008 | Kasahara |
| 2008/0177302 | A1 | 7/2008 | Shurnas |
| 2008/0269806 | A1 | 10/2008 | Zhang et al. |
| 2009/0036893 | A1 | 2/2009 | Kartalian et al. |
| 2009/0076617 | A1 | 3/2009 | Ralph et al. |
| 2009/0171397 | A1* | 7/2009 | Rothman ............ A61B 17/8042 606/280 |
| 2009/0210010 | A1 | 8/2009 | Strnad et al. |
| 2009/0222047 | A1 | 9/2009 | Graham |
| 2009/0254190 | A1 | 10/2009 | Gannoe et al. |
| 2010/0036430 | A1 | 2/2010 | Hartdegen et al. |
| 2010/0094294 | A1 | 4/2010 | Gillard et al. |
| 2010/0094428 | A1* | 4/2010 | Ralph .................. A61B 17/688 623/17.19 |
| 2010/0106110 | A1 | 4/2010 | De Luca |
| 2010/0125297 | A1 | 5/2010 | Guederian et al. |
| 2010/0152752 | A1 | 6/2010 | Denove et al. |
| 2010/0211071 | A1 | 8/2010 | Lettmann et al. |
| 2010/0211075 | A1 | 8/2010 | Stone |
| 2010/0234896 | A1 | 9/2010 | Lorenz et al. |
| 2010/0249687 | A1 | 9/2010 | Goswami et al. |
| 2010/0262194 | A1 | 10/2010 | Wagner et al. |
| 2011/0061664 | A1 | 3/2011 | Paris Mayans Carlos |
| 2011/0077656 | A1 | 3/2011 | Sand et al. |
| 2011/0082405 | A1 | 4/2011 | Domangue et al. |
| 2011/0118780 | A1 | 5/2011 | Holmes, Jr. |
| 2011/0119807 | A1 | 5/2011 | DellaCorte et al. |
| 2011/0130789 | A1 | 6/2011 | Shurnas et al. |
| 2011/0178557 | A1 | 7/2011 | Rush et al. |
| 2011/0224729 | A1 | 9/2011 | Baker |
| 2011/0301648 | A1 | 12/2011 | Lofthouse et al. |
| 2012/0016426 | A1 | 1/2012 | Robinson |
| 2012/0071935 | A1 | 3/2012 | Keith et al. |
| 2012/0215147 | A1 | 8/2012 | Lunnon |
| 2012/0330322 | A1 | 12/2012 | Sand et al. |
| 2016/0157904 | A1 | 6/2016 | Zeetser et al. |

OTHER PUBLICATIONS

Nov. 24, 2014, International Search Report and Written Opinion for International Application No. PCT/US2014/046824 Filed Jul. 16, 2014.

* cited by examiner

METHOD AND DEVICE FOR CORRECTING BONE DEFORMITIES

INCORPORATION BY REFERENCE TO ANY PRIORITY APPLICATIONS

This application is a continuation of PCT Application No. PCT/US2013/050687, filed on Jul. 16, 2013, which claims priority benefit of U.S. Provisional Application No. 61/672,297 filed on Jul. 17, 2012, U.S. Provisional Application No. 61/713,443 filed on Oct. 12, 2012, and to U.S. application Ser. No. 13/720,826, filed Dec. 19, 2012. Each of these applications is hereby incorporated by reference in its entirety.

BACKGROUND OF THE INVENTION

Field of the Invention

Embodiments of the invention relate to surgical implant devices for repairing angular bone deformities, in particular, metatarsus primus adductus. While certain embodiments of the invention were conceived for the purposes of correcting metatarsus primus adductus, it is conceivable that other embodiments can be adapted to correct other bone deformities as long as there is a stable bone somewhat adjacent to an unstable bone.

Description of the Related Art

Metatarsus primus adductus is a progressive angular deformity in the foot, between the first and second metatarsals, when the unstable or hypermobile first metatarsal deviates medially, increasing the intermetatarsal angle between the first and second metatarsals Surgical procedures to correct this condition are chosen based on the severity of the angular deformity. Traditionally, surgical correction of moderate to severe angular deformities between the first and second metatarsals involves bone remodeling, osteotomies, wedge resection of bone or joint fusions, which cause irreversible alterations to bone and joint structures. A more desirable technique is to anatomically correct the deformity by reducing the abnormally wide angle between the two metatarsals by tethering them closer together using suture like material. Known are U.S. Pat. Nos. 8,221,455, 7,901,431, 7,875,058, 5,529,075, and U.S. Patent Application No. 2011/0224729.

U.S. Pat. Nos. 8,221,455, 7,901,431, 7,875,058 and U.S. Patent Application No. 2011/0224729 are tethering techniques whereby fiberwire, a suture-like material, along with buttress plates and/or buttons are used to tether the first and second metatarsals closer together like a tightrope. These techniques require holes to be drilled through both the first and second metatarsals. The Mini Tightrope system by Arthrex is an example of the tethering technique. First, a hole is drilled through the first and second metatarsals. Next, a buttress plate is secured to the second metatarsal bone by passing the suture through holes in the plate and through holes in both bones, then reducing the angular deformity by tightening the suture using a button and suture knot located on the medial side of the first metatarsal. The Mini Tightrope FT system by Arthrex is another example of tethering technique which uses an anchor-suture-button complex, where a threaded anchor is drilled into the second metatarsal base and the suture thread is then passed through a hole in the first metatarsal and the angular deformity is reduced as the suture thread is tightened and secured with a suture knot and button located along the medial aspect of the first metatarsal. Both of these tethering techniques require drilling into both the second and first metatarsals. U.S. Pat. No. 5,529,075 is similar in that it too requires drilling through the first and second metatarsals. Instead of a flexible suture-anchor technique, this reference requires the installation of a rigid stabilizing member between the first and second metatarsal. However, each of these references suffers from one or more of the following disadvantages: a hole must be drilled into or through the second metatarsal, to secure one end of the tethering device while the other (medial) end of the tethering device is secured with a button.

Drilling a hole through the second metatarsal, which is significantly smaller in diameter by comparison to the first metatarsal, severely weakens the bone. To minimize weakening of the second metatarsal, the hole must be drilled through the centerline of the bone so that a maximum amount of bone remains above and below the hole. Nevertheless, drilling a hole through the centerline of the second metatarsal is especially difficult because it is done at an angle through a hole in the first metatarsal. Making the procedure more difficult, the drilling must be done with little or no visibility. A second metatarsal bone which has been drilled through is more vulnerable to stress and/or fracture from tension caused by the tethering techniques. Fracture of the second metatarsal is a common and potentially devastating complication of these tethering techniques. Additionally, the use of buttons and suture knots located along the medial aspect of the first metatarsal can cause irritation of tissue, knot loosening and skin irritation/breakdown from prominent components.

Some surgeons have attempted to avoid drilling into the second metatarsal via a modification of the tethering technique, known as lasso technique. With the lasso technique, no holes are drilled through the second metatarsal, and no buttress plate or button is used. Instead, suture tape (i.e. Fibertape) is tied around the second metatarsal in the form of a cow-hitch knot and then secured to the first metatarsal. While the lasso technique avoids drilling through the second metatarsal by instead looping suture tape around the metatarsal, the suture tie itself can cause periosteal reaction and bone callus formation in some patients due to friction between the suture tape and the bone. To avoid periosteal reaction, few surgeons use absorbable suture to tether the first and second metatarsals together, but once the suture finally absorbs there is likely some loss of correction and possible recurrence of angular deformity.

Because of the aforementioned problems, there is a need for method and device for reducing angular bone deformities between two bones, using a tethering technique with a suture material which not only avoids the complications associated with drilling into the second metatarsal, but also avoids the friction and tension forces (i.e. rope-burn) associated with lasso-type techniques and which also avoids the complications associated with the prominent medial button and suture knot.

SUMMARY OF THE INVENTION

Embodiments of the present invention satisfy this need in the form of a method and device that allows for the correction and reduction of angular deformities such as metatarsus primus adductus using a tethering technique which does not require drilling into the second metatarsal, nor does it require the placement of a prominent suture knot/button device medially along the first metatarsal.

In one embodiment, a winged looped plate comprises a plate body with winged buttresses and dorsal loop. The winged looped plate with incorporated dorsal loop can be affixed to a bone without any drilling or violating of the bone. With the plate against the bone cortex, a cerclage technique can be used to loop cerclage material, such as suture tape, fibertape, or wire, around the plate and bone. The cerclage material is passed through the dorsal loop of the plate to keep the cerclage material centered on the plate. The cerclage material is tied around the second metatarsal using a lasso-type or cowhitch-type tie. Then, upon tightening the cerclage, the plate would be affixed to the bone under tension, thereby dispensing with the need to affix the plate to the bone with screws or drilled holes. The other end of the tethering mechanism can then be fixated to the first metatarsal (with the angular deformity anatomically reduced) using knotless anchors (interference screws) thus avoiding the use of prominent buttons and suture knots that are components of all other comparative tethering methods. By using a cerclage technique to affix the winged looped plate to bone under tension, the second metatarsal is protected not only from drill hole related stress fractures, but also from friction/shear forces (cortical reaction) associated with tying suture around bone and directly against the bone cortex without any shielding.

This method and device addresses the aforementioned existing problem of angular bone deformities, in particular metatarsus primus adductus, the underlying cause of hallux valgus/bunion deformities, by utilizing the winged looped plate of embodiments described herein, placed directly against the second metatarsal bone.

The winged looped plate allows the surgeon to tie cerclage material around the plate, protecting the bone from both friction and tension forces and eliminating need for drilling through the second metatarsal. The method uses the winged looped plate, cerclage material, a suture passing instrument and two tenodesis (interference) screws to achieve a true reduction of the angular deformity. The two bones are tethered together using a cerclage technique with the winged looped plate protecting the second metatarsal, while knotless anchors are used in the first metatarsal. This method creates a button-less, knotless, fully adjustable and reversible angular deformity correction, while the plate protects the second metatarsal bone from harmful tension and friction.

While embodiments of the invention were conceived for the purposes of correcting metatarsus primus adductus, it is conceivable that embodiments can be adapted to correct other bone deformities as long as there is a stable bone somewhat adjacent to an unstable bone.

In accordance with one aspect, a winged looped plate device comprises an at least semi-tubular plate body with a convex outer surface and concave inner surface; at least one buttress wing extending perpendicularly from a longitudinal axis of the plate body, continuing the at least semi-tubular shape of the plate body; and at least one dorsal loop disposed on the convex outer surface of the plate body for threading of cerclage material through the dorsal loop and tied around the device and a bone such that tension applied to the cerclage material secures the plate to the bone to prevent displacement of the plate body.

In some embodiments, the plate body comprises at least one hole for ingrowth of tissue. In some embodiments, the at least one buttress wing comprises at least one hole for ingrowth of tissue. In some embodiments, the plate body comprises at least one opening for a set screw. In some embodiments, the at least one buttress wing comprises at least one opening for a set screw. In some embodiments, the at least one dorsal loop is disposed on the convex outer surface of the plate body at a point where the buttress wing and plate body intersect so that tension is applied evenly when cerclage material is used to secure the plate body to the bone to prevent displacement of the plate body. In some embodiments, the device further comprises a length of cerclage material. In some embodiments, the position of the dorsal loop is fixed with respect to the plate body.

In accordance with another aspect, a device for correcting angular deformity between first and second metatarsals of a human foot comprises an at least semi-tubular plate body with a convex outer surface and concave inner surface; at least one buttress wing extending perpendicularly from a longitudinal axis of the plate body, continuing the at least semi-tubular shape of the plate body, wherein the plate body is configured to receive the second metatarsal therein, such that the concave inner surface abuts a lateral surface of the second metatarsal, and the at least one buttress wing extends over and abuts an upper or lower surface of the second metatarsal towards the first metatarsal, at least one dorsal loop disposed on the convex outer surface of the plate body, wherein the dorsal loop is configured to receive cerclage material therethrough extending in a direction substantially orthogonal to the longitudinal axis of the plate body towards the first metatarsal, such that coupling the cerclage material to the first metatarsal and tightening the cerclage material secures the plate to the second metatarsal and moves the first and second metatarsals towards one another.

In some embodiments, the device comprises two buttress wings extending from opposite sides of the plate body, each of the buttress wings continuing the at least semi-tubular shape of the plate body. In some embodiments, the position of the dorsal loop is fixed with respect to the plate body. In some embodiments, the dorsal loop is disposed substantially centrally between first and second lateral portions of the plate body and substantially aligned with the buttress wing. In some embodiments, the device further comprises a length of cerclage material.

In accordance with another aspect, a bone stabilization device comprises an elongated plate body comprising: a first surface facing in a first direction configured to face the bone; a second surface facing in a second direction; distal and proximal ends; and first and second lateral portions extending between the distal and proximal ends; a buttress wing extending from the first lateral portion at least partially along the first direction; a dorsal loop disposed on the second surface of the plate body, the dorsal loop disposed substantially centrally between the first and second lateral edges and substantially aligned with the buttress wing, wherein the dorsal loop extends substantially along the longitudinal axis of the plate body, defining an aperture configured to receive cerclage material therethrough extending in a direction substantially orthogonal to the longitudinal axis of the plate body.

In some embodiments, the plate is semi-tubular. In some embodiments, the first surface is concave. In some embodiments, the second surface is convex. In some embodiments, the buttress wing extends curvature of the semi-tubular plate. In some embodiments, the curvature of the semi-tubular plate is configured to receive a second metatarsal bone of human foot therein. In some embodiments, the bone stabilization device comprises at least one hole on the plate body. In some embodiments, the bone stabilization device further comprises a length of cerclage material.

In some embodiments, a bone stabilization kit comprises the bone stabilization device, a length of cerclage material, a plurality of tenodesis screws, and a suture-passing instrument. In some embodiments, the cerclage material comprises at least one of: suture tape, fibertape, or wire.

In accordance with another aspect, a method of bone stabilization between an unstable bone and a stable bone comprises providing a bone stabilization device comprising a plate body with a convex outer surface and a concave inner surface; at least one buttress wing extending perpendicularly from a longitudinal axis of the plate body; and at least one dorsal loop disposed on the convex outer surface of the plate body, the method further comprising disposing the bone stabilization device such that the concave inner surface of the plate body abuts the stable bone; passing cerclage material through the dorsal loop and coupling it to the unstable bone; and tightening the cerclage material.

In some embodiments, the unstable bone is a first metatarsal bone and the stable bone is a second metatarsal bone. In some embodiments, the method further comprises securing the cerclage material to the unstable bone. In some embodiments, the method further comprises passing a free end of the cerclage material into a hole drilled into the unstable bone, and inserting a tenodesis screw into the drilled hole to secure the cerclage material. In some embodiments, tightening the cerclage material reduces an angle between the stable and unstable bones.

In accordance with another aspect, a method of correcting bone deformities such as metatarsus primus adductus comprises making a medial incision along a first metatarsal; drilling a hole through the first metatarsal; making a dorsal incision over a second metatarsal; creating a tunnel through soft tissue between the first metatarsal and the second metatarsal, connecting the dorsal and medial incisions; passing cerclage material into the medial incision, through the tunnel, and out through the dorsal incision; threading the cerclage material through a dorsal loop of a bone stabilization plate; disposing the plate against a lateral cortex of the second metatarsal; tying the cerclage material around the second metatarsal and the plate in a cerclage fashion and tightening the cerclage material; passing free ends of the cerclage material back through the tunnel from lateral to medial and pulling the free ends of the cerclage material through the hole in the first metatarsal; applying tension to the cerclage material while reducing the angular deformity between the first and second metatarsal; and inserting a tenodesis screw medially in the hole of the first metatarsal fixating the cerclage material to the first metatarsal under desired tension.

In some embodiments, the free ends of the cerclage material are pulled through a second drill hole in the first metatarsal and secured with a second tenodesis screw for additional cerclage material tension and for stabilization. In some embodiments, a set screw is inserted through a single hole in the dorsal wing of the plate, and inserted only through the dorsal cortex of the metatarsal.

In accordance with another aspect, a method of correcting angular bone deformity between first and second metatarsal bones comprises: providing a plate body with a convex outer surface and a concave inner surface, the plate body having a dorsal loop disposed on the convex outer surface; disposing the plate body such that the concave inner surface abuts a lateral side of the second metatarsal bone; passing cerclage material through the dorsal loop and coupling it to the first metatarsal bone; and tightening the cerclage material to decrease the angular bone deformity.

In some embodiments, the method further comprises securing the cerclage material to the first metatarsal bone using a tenodesis screw. In some embodiments, the free ends of the cerclage material are pulled through a second drill hole in the first metatarsal bone and secured with a second tenodesis screw. In some embodiments, a screw is inserted through a hole in the plate and into the dorsal cortex of the second metatarsal bone.

DETAILED DESCRIPTION OF THE PREFERRED EMBODIMENTS

Figure 1:
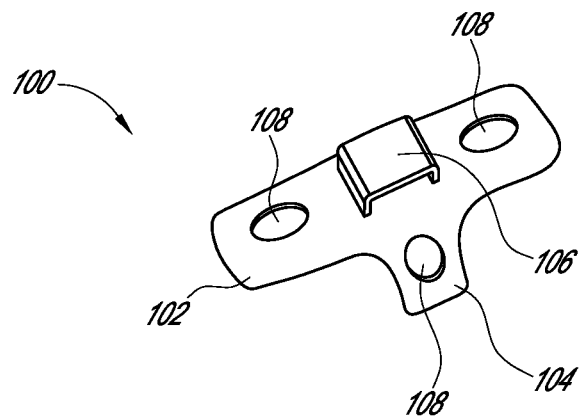
FIG. 1 is a perspective view of a device embodying features of a method and device for correcting bone deformities such as metatarsus primus adductus.
Figure 2:
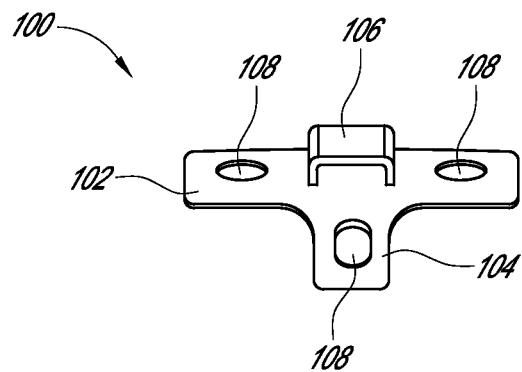
FIG. 2 is a side profile view of a device embodying features of a method and device for correcting bone deformities such as metatarsus primus adductus.
Figure 3:
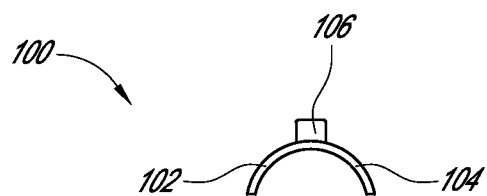
FIG. 3 is a front profile view of a device embodying features of a method and device for correcting bone deformities such as metatarsus primus adductus.
Figure 10:
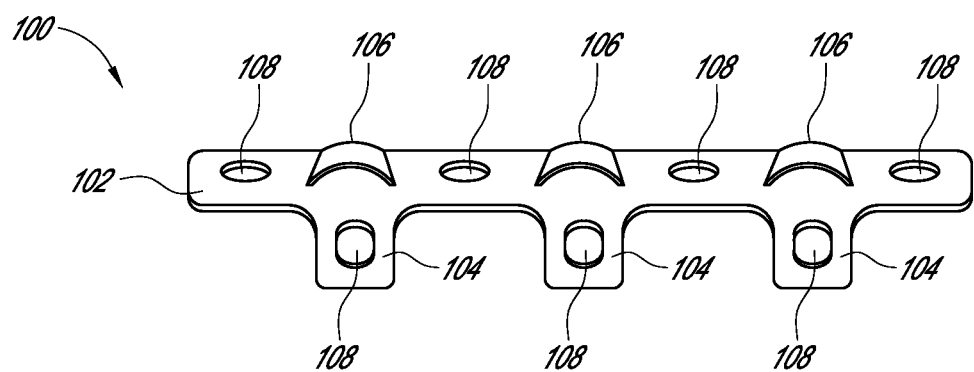
FIG. 10 is an alternate embodiment of the winged looped plate device embodying features for protection of a long bone when using any cerclage technique in a series as may be necessary for longer bones. An elongated version of the winged looped plate allows for multiple wings and multiple loops for applying a series of cerclage ties over a longer bone. This figure also shows a possible low-profile variation of the loops if the cerclage material is thinner (i.e. monofilament wire).

FIGS. 1-3 illustrate one embodiment of the winged looped plate 100 device to correct bone deformities, in particular metatarsus primus adductus, the underlying cause of hallux valgus/bunion deformities. The winged looped plate 100 comprises a plate body 102 which in some embodiments is semi-tubular or tubular, with buttress wings 104, a dorsal loop 106, and ingrowth holes 108. Depending on where the plate is to be used, the number of buttress wings 104, the number and shape of the dorsal loops 106, and size and number of holes 108 on the plate body can be customized. For example, several sets of buttress wings 104, dorsal loops 106, and ingrowth holes 108 can be arranged in series along a plate body for use in longer bones when a series of cerclage ties are needed. (FIG. 10). The plate body 102 in some embodiments is semi-tubular in shape with a convex outer surface and concave inner surface to distribute forces of the suture tape evenly and avoid the need to drill a hole through the bone. The plate body 102 comprises extension buttress wings 104 which follow the semi-tubular shape of the plate body to protect the adjacent bone cortices where suture tape wraps around the device and bone. The plate body 102 and buttress wings 104 may have ingrowth holes 108 to allow bony and soft tissue/scar tissue ingrowth for long-term fixation and stability of the plate position. The dorsal loop 106 extends from the outer convex surface of the plate body 102 to facilitate the threading of cerclage material, such as suture tape, fibertape, or wire, around the device. The dorsal loop 106 retains the cerclage material centered on the plate upon tightening to evenly secure the plate firmly against the bone under tension.

Embodiments can be fabricated to comprise the plate body 102, buttress wings 104, dorsal loop 106, and holes 108 using conventional manufacturing methods such as welding, pressing, casting, machining and/or forging. A variety of materials may be used including, metallics (i.e. titanium, stainless steel), bio absorbables (i.e. Poly-L-Lactide PLLA) or non-absorbables (i.e. PEEK polymer). Additionally, the inner surface of the winged looped plate 100 could be plasma coated or otherwise roughened for enhanced grip to bone.

Figure 4:
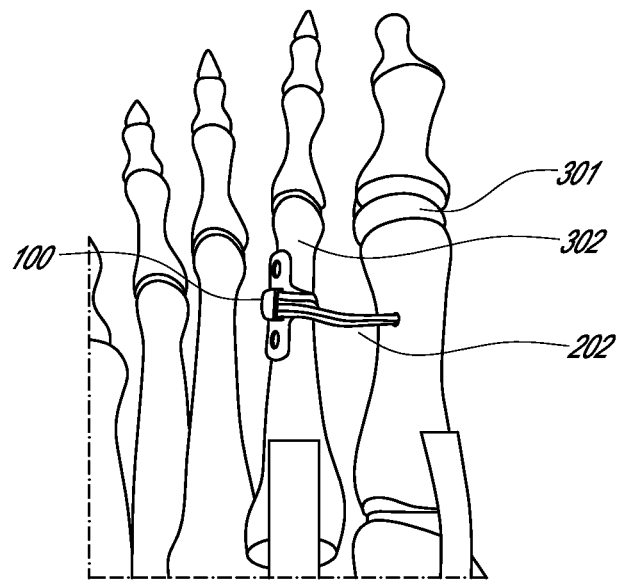
FIG. 4 is a top view of a skeleton embodying features of a method and device for correcting bone deformities such as metatarsus primus adductus.
Figure 5:
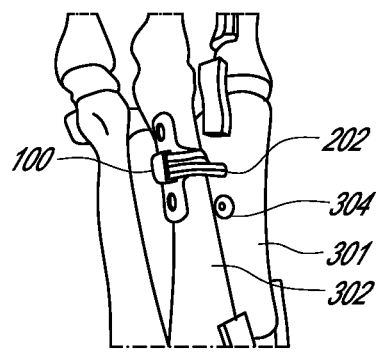
FIG. 5 is a profile view from the second metatarsal of a skeleton embodying features of a method and device for correcting bone deformities such as metatarsus primus adductus.
Figure 6:
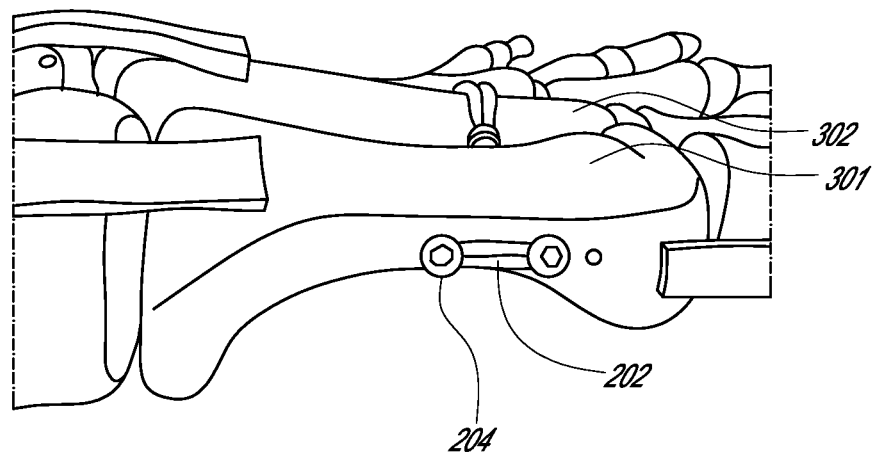
FIG. 6 is a profile view from the first metatarsal of a skeleton embodying features of a method and device for correcting bone deformities such as metatarsus primus adductus.
Figure 9:
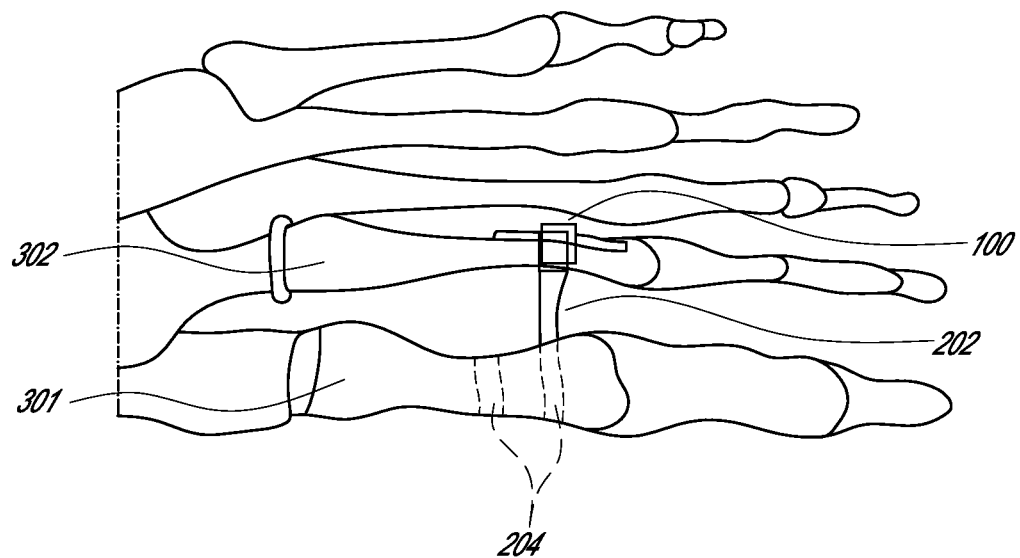
FIG. 9 is an illustration of the bone deformity, metatarsus primus adductus, anatomically reduced after the device and method is applied.
Figure 11:
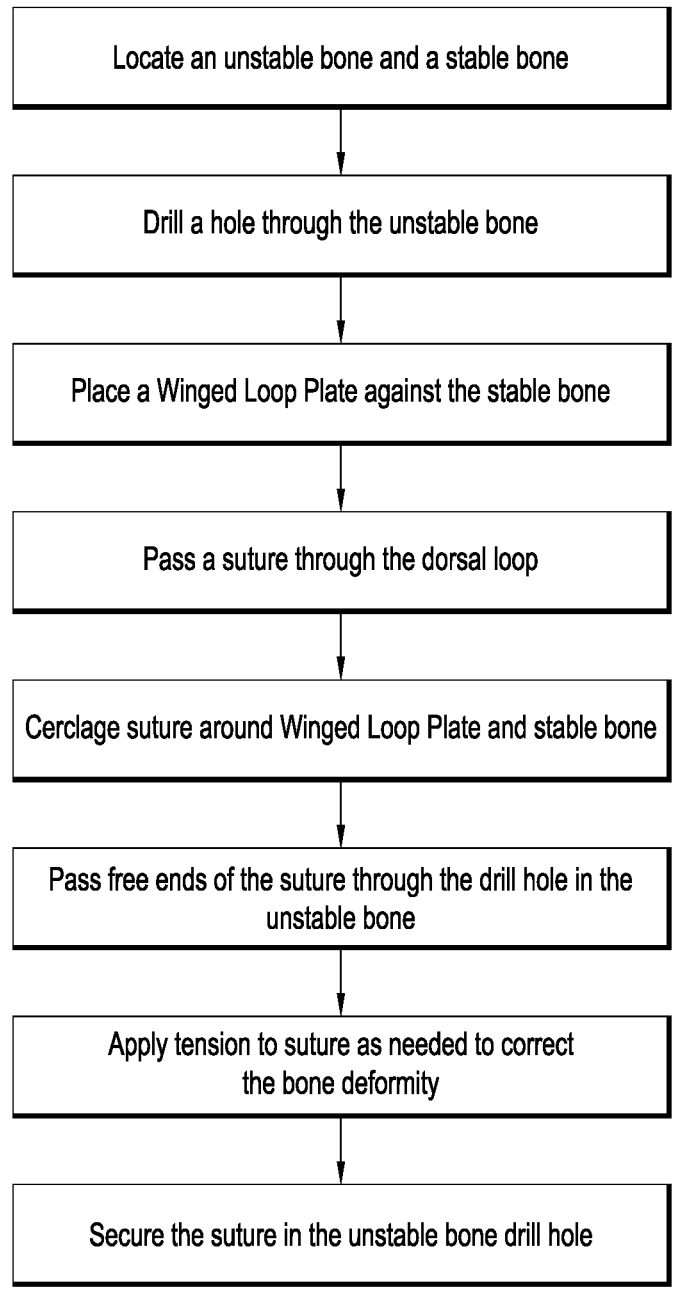
FIG. 11 is a flowchart illustrating a method for the correction of a bone deformity.

FIG. 11 is a flowchart illustrating the correction of a bone deformity using the method and device. First, an unstable bone 301 and a stable bone 302 near the unstable bone 301 is located (FIG. 4). Second, a hole to accommodate a tenodesis (interference type) screw 204 is drilled through the unstable bone 301 (FIG. 5) so that an opening is formed on the side of the unstable bone that is furthest away from the stable bone (FIG. 9). Third, a winged looped plate 100 is placed with the inner surface against the stable bone 302 and with the dorsal loop 106 furthest away from the unstable bone 301 (FIG. 5). Fourth, a cerclage material 202 is passed through the dorsal loop 106 of the winged looped plate 100 on the stable bone 302 and tied around the stable bone 302 and winged looped plate 100 using a cerclage technique (FIG. 5). Fifth, the free ends of the cerclage material 202 are passed through the hole in the unstable bone 301 and tension is applied to the suture 202 to reduce the angular bone deformity (FIG. 6). Sixth, the cerclage material 202 is secured to the unstable bone 301 using a tenodesis (interference-type) screw 204 in the drill hole (FIG. 6).

Figure 7:
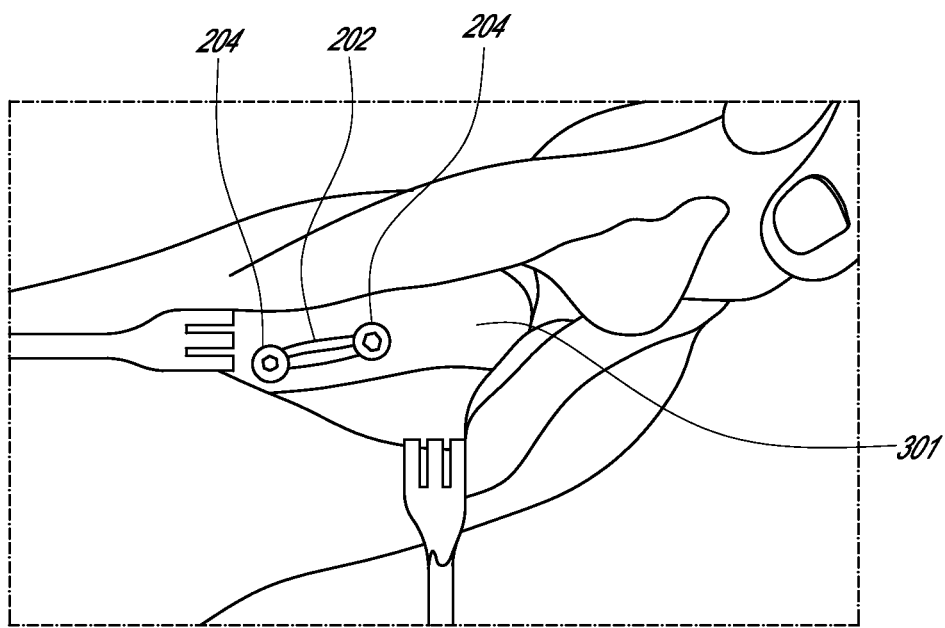
FIG. 7 is a profile view of a medial incision made along the first metatarsal with tenodesis (interference) screws anchoring the suture tape to the first metatarsal.

FIGS. 4-9 illustrate a method of using a winged looped plate 100 to correct the angular bone deformity, metatarsus primus adductus. First, a medial incision is made along the first metatarsal 301 (the unstable bone) head and neck as best illustrated in FIG. 7. Second, a small incision is made dorsally over the second metatarsal 302 (the stable bone) neck. Third, blunt dissection is used to create a tunnel through the soft tissue between the first metatarsal 301 and second metatarsal 302, connecting the two incisions. Third, cerclage material 202 is passed through the tunnel from medial to lateral, and located through the dorsal incision where it is then threaded through the dorsal loop 106 of the winged looped plate 100, which is then placed against the lateral cortex of the second metatarsal before the cerclage material 202 is tied once around the second metatarsal 302 using a cerclage technique, as best illustrated in FIGS. 4-5.

Fourth, the cerclage material 202 is tightened so that the winged looped plate 100 is pressed firmly against the lateral aspect of the second metatarsal 302 and that buttress wings 104 of the plate cover and protect the dorsal and plantar cortices of the second metatarsal 302. The plate would be adhered to the bone primarily via tension from tightening the suture tape cerclage however, additional forms of optional fixation may include a single setscrew through a hole 108 in the dorsal wing 104, bone glue/paste/putty or other fixatives.

Figure 8:
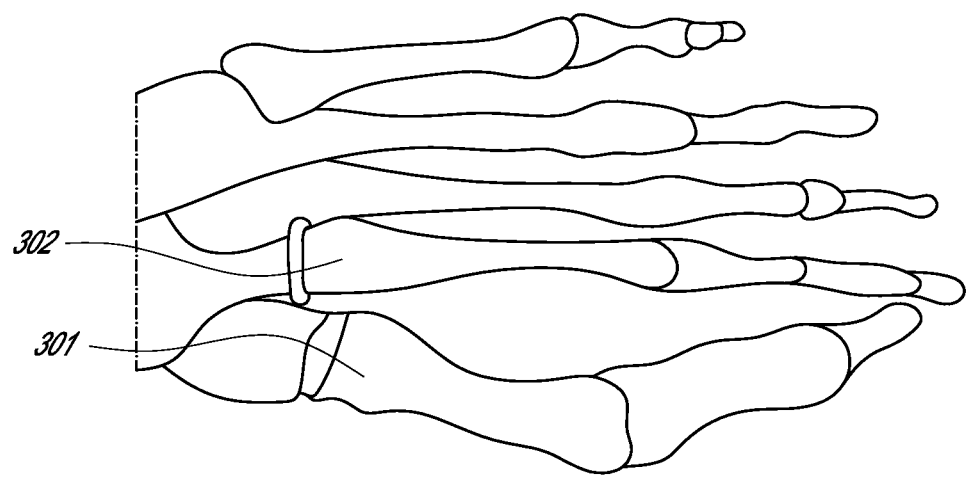
FIG. 8 is an illustration of the bone deformity, metatarsus primus adductus, before the device and method is applied.

Fifth, the free ends of the cerclage material 202 are then passed back through the soft tissue tunnel medially, then through a drill hole in the first metatarsal 301, from lateral to medial as illustrated in FIGS. 6-7. Sixth, the cerclage material 202 is pulled tightly through the drill hole, reducing the angular deformity to a more anatomic position, as illustrated in FIGS. 8-9. Seventh, a tenodesis anchor screw 204, shown in FIGS. 6-7, is inserted into the drill hole as an interference screw to maintain tension across the tethering mechanism between the first and second metatarsals. Finally, a second point of fixation can be achieved by passing the remaining cerclage material 202 end through a second drill hole in the first metatarsal and inserting a second tenodesis screw 204.

All features disclosed in this specification, including any accompanying claim, abstract, and drawings, may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. §112, paragraph 6. In particular, the use of "step of" in the claims herein is not intended to invoke the provisions of 35 U.S.C. §112, paragraph 6.

Although preferred embodiments have been shown and described, various modifications and substitutions may be made thereto without departing from the spirit and scope of the invention. Accordingly, it is to be understood that the present invention has been described by way of illustration and not limitation.

What is claimed is:

1. A metatarsal bone stabilization device, comprising:
   an elongate body configured to extend along a length of a patient's metatarsal bone, the elongate body comprising a first end and a second end and a longitudinal axis extending between the first end and the second end;
   two buttress wings, each extending away from an opposite side of the elongate body such that longitudinal axes of both buttress wings extend within a common transverse plane that is perpendicular to the longitudinal axis of the elongate body, wherein inner surfaces of the buttress wings at least partially face each other and are configured so that when the elongate body and the buttress wings are placed against the patient's metatarsal bone, the patient's metatarsal bone is at least partially surrounded by the elongate body and the two buttress wings; and
   a channel formed by fixed and immobile surfaces on the device and defining a path substantially perpendicular to the longitudinal axis of the elongate body and directly aligned with the common transverse plane, the channel being configured such that when the elongate body and the two buttress wings are placed against the patient's metatarsal bone and cerclage material passes along the channel and is circumferentially tied around the elongate body and the underlying metatarsal bone to secure the cerclage material to an adjacent bone of the patient, the cerclage material extends directly over each of the two buttress wings.

2. The metatarsal bone stabilization device of claim 1, wherein the channel is located on the elongate body.

3. The metatarsal bone stabilization device of claim 1, wherein the elongate body comprises an elongate plate.

4. The metatarsal bone stabilization device of claim 1, wherein the channel forms a transverse aperture on the elongate body.

5. The metatarsal bone stabilization device of claim 1, wherein the elongate body and the two buttress wings have inner surfaces that are concave and outer surfaces that are convex.

6. The metatarsal bone stabilization device of claim 1, further comprising one or more holes in the elongate body.

7. The metatarsal bone stabilization device of claim 1, further comprising one or more holes in the two buttress wings.

8. The metatarsal bone stabilization device of claim 1, wherein the channel and the two buttress wings are centrally located between the first end and the second end of the elongate body.

9. The metatarsal bone stabilization device of claim 1, wherein the cerclage material extends entirely along the longitudinal axis of the two buttress wings.

10. The metatarsal bone stabilization device of claim 1, wherein the buttress wings are configured to shield the bone by preventing cerclage material from directly contacting the bone on the side of tension, and partially along adjacent cortices, thereby reducing a total area of contact between the cerclage material and underlying bone when cerclage material extends through the channel to secure the cerclage material around the plate and the patient's bone.

* * * * *